United States Patent [19]

Hall et al.

[11] Patent Number: 4,526,900

[45] Date of Patent: Jul. 2, 1985

[54] 7-OXABICYCLOHEPTANE SUBSTITUTED OXA PROSTAGLANDIN ANALOGS AND THEIR USE IN THE TREATMENT OF THROMBOLYTIC DISEASE

[75] Inventors: Steven E. Hall, Ewing Township, Mercer County; Martin F. Haslanger, Lambertville, both of N.J.

[73] Assignee: E. R. Squibb & Sons, Inc., Princeton, N.J.

[21] Appl. No.: 574,000

[22] Filed: Jan. 26, 1984

[51] Int. Cl.³ .................. A61K 31/557; C07D 307/00
[52] U.S. Cl. ..................................... 514/469; 549/463
[58] Field of Search ......................... 549/463; 424/285

[56] References Cited

U.S. PATENT DOCUMENTS

| | | | |
|---|---|---|---|
| 4,143,054 | 3/1979 | Sprague | 549/463 |
| 4,187,236 | 2/1980 | Sprague | 549/463 |
| 4,220,594 | 9/1980 | Sprague | 549/463 |
| 4,228,180 | 10/1980 | Sprague | 549/463 |
| 4,254,044 | 3/1981 | Sprague | 549/463 |

FOREIGN PATENT DOCUMENTS 0043292 8/1982 European Pat. Off. .
2039909 8/1980 United Kingdom .

Primary Examiner—Henry R. Jiles
Assistant Examiner—Bernard I. Dentz
Attorney, Agent, or Firm—Lawrence S. Levinson; Burton Rodney

[57] ABSTRACT

7-Oxabicycloheptane substituted oxo prostaglandin analogs are provided having the structural formula

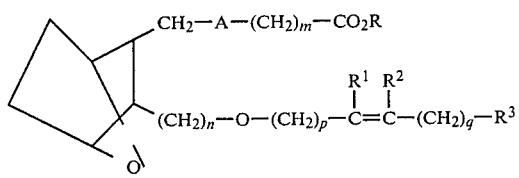

wherein R is hydrogen, lower alkyl, alkali metal or tris(hydroxymethyl)aminomethane, $R^1$ and $R^2$ may be the same or different and are hydrogen or lower alkyl, $R^3$ is hydrogen, lower alkyl, aryl or cycloalkyl, A is —CH=CH— or —(CH$_2$)$_2$—, m is 1 to 8, and n is 1 to 4, p is 1 to 12 and q is 0 to 5, and including all stereoisomers thereof.

The compounds are cardiovascular agents useful, for example, in the treatment of thrombolytic disease.

21 Claims, No Drawings

7-OXABICYCLOHEPTANE SUBSTITUTED OXA PROSTAGLANDIN ANALOGS AND THEIR USE IN THE TREATMENT OF THROMBOLYTIC DISEASE

DESCRIPTION OF THE INVENTION

The present invention relates to 7-oxabicycloheptane oxaprostaglandin analogs which are cardiovascular agents useful, for example, in the treatment of thrombolytic disease. These compounds have the structural formula

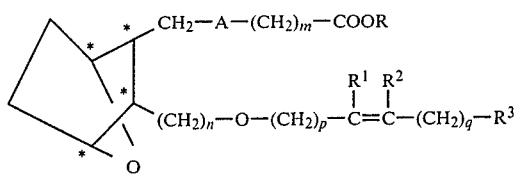   I and including all stereoisomers thereof, wherein
A is CH=CH or $(CH_2)_2$,
m is 1 to 8,
n is 1 to 4,
p is 1 to 12,
q is 0 to 5,
R is H, lower alkyl, alkali metal or tris(hydroxymethyl)aminomethane,
$R^1$ and $R^2$ may be the same or different and are hydrogen or lower alkyl, and
$R^3$ may be hydrogen, lower alkyl, aryl or cycloalkyl.

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an aryl substituent (that is, aralkyl), an alkoxy substituent, a haloaryl substituent, an alkyl-aryl substituent, a cycloalkyl substituent (that is, cycloalkylalkyl) or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 halogens, 1 or 2 lower alkyl groups and/or lower alkoxy groups.

The term "aralkyl", "aryl-alkyl" or "aryl-lower alkyl" as used herein refers to lower alkyl groups as discussed above having an aryl substituent, such as benzyl.

The term "halogen" or "halo" as used herein refers to chlorine, bromine, fluorine or iodine with chlorine being preferred.

The terms "$(CH_2)_m$", "$(CH_2)_n$", "$CH_2)_p$" and "$(CH_2)_q$" include a straight or branched chain radical having from 1 to 8 carbons in the normal chain in the case of "$(CH_2)_m$", 1 to 4 carbons in the normal chain in the case of "$(CH_2)_n$", 1 to 12 carbons in the normal chain in the case of "$(CH_2)_p$" and 0 to 5 carbons in the normal chain in the case of "$(CH_2)_q$" and may contain one or more lower alkyl substituents. Examples of $(CH_2)_m$, $(CH_2)_n$, $(CH_2)_p$ and $(CH_2)_q$ groups include $CH_2$, $CH_2CH_2$, $(CH_2)_3$, $(CH_2)_4$, $(CH_2)_5$, $(CH_2)_6$, $(CH_2)_7$,

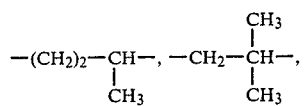

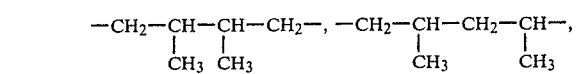

and the like.

Preferred are those compounds of formula I wherein A is $(CH_2)_2$ or CH=CH, m is 2 to 5, R is H, n is 1, 2 or 3, p is 1 to 8, q is 0 to 3, $R^1$ and $R^2$ are hydrogen and/or methyl, $R^3$ is methyl, ethyl, hydrogen, propyl, cyclohexyl, cyclohexylmethyl, phenyl, benzyl, 2-phenylethyl or 3-phenylpropyl.

The various compounds of the invention may be prepared as outlined below.

A. Where n = 1 and A is —CH=CH—

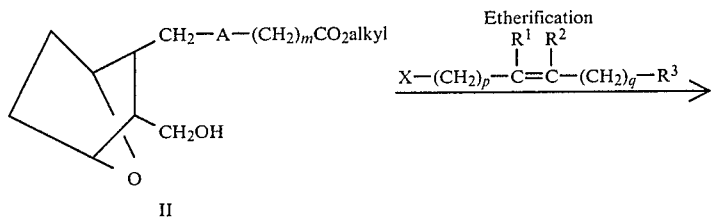

-continued
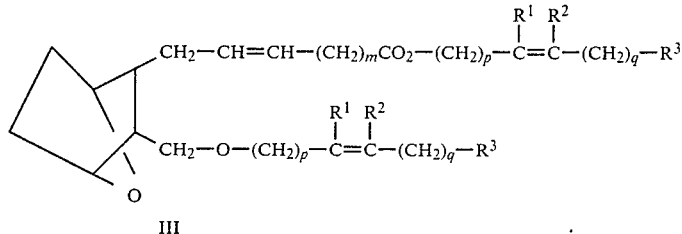
III
B. Where n = 1 and A is —(CH$_2$)$_2$—
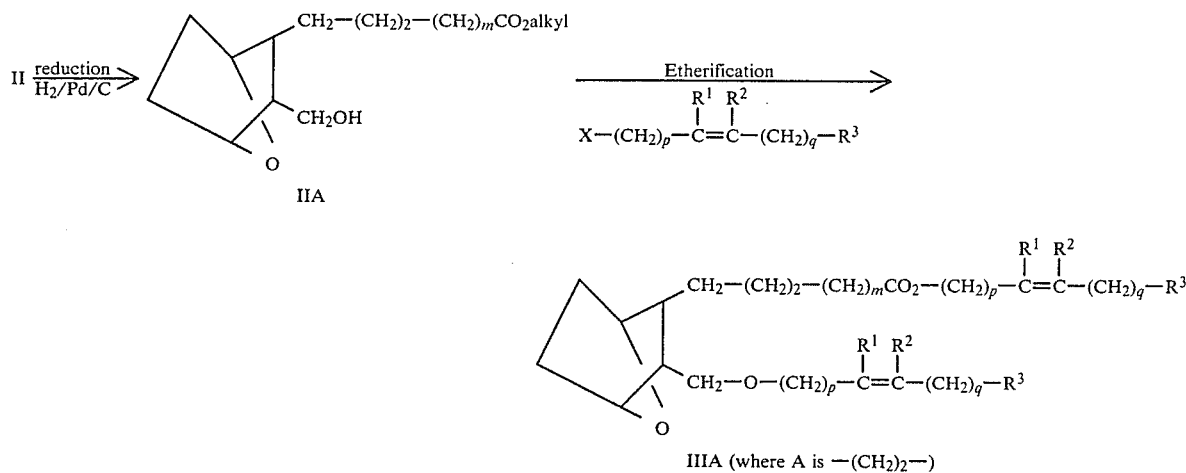
IIIA (where A is —(CH$_2$)$_2$—)
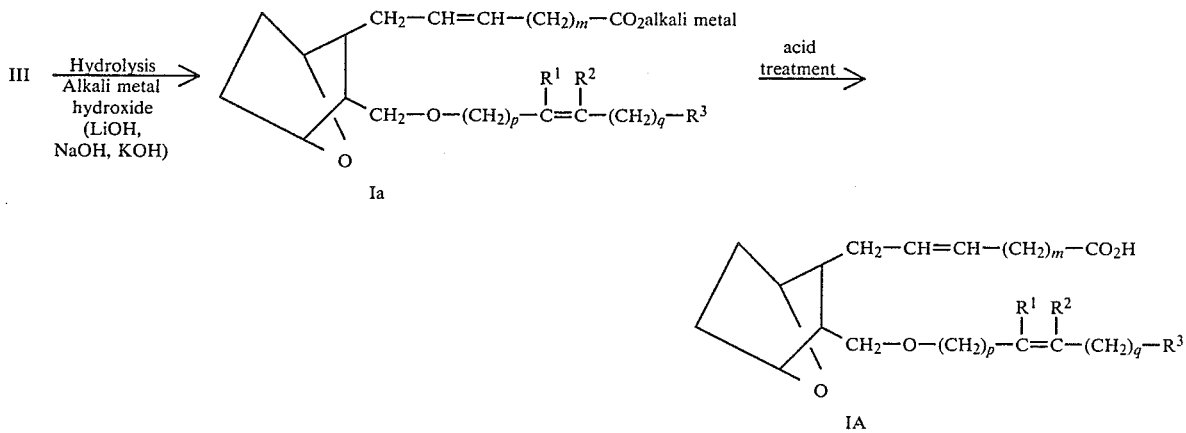
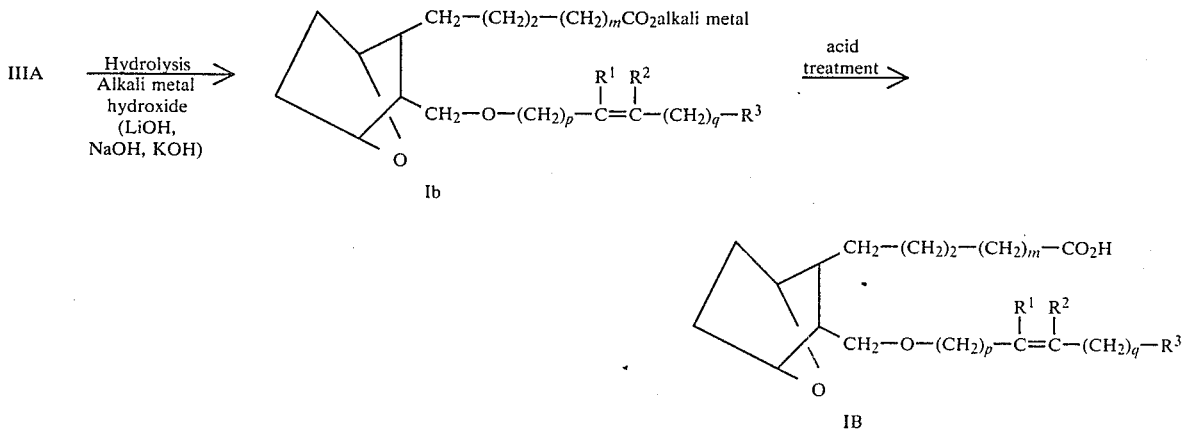
C. Where n is 2 to 4

-continued
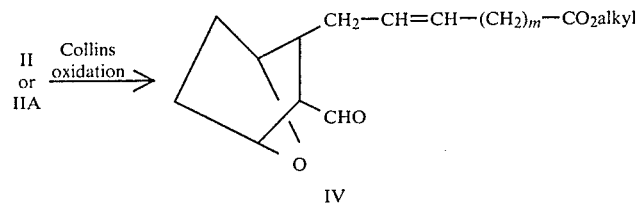
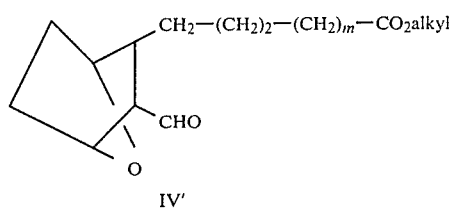
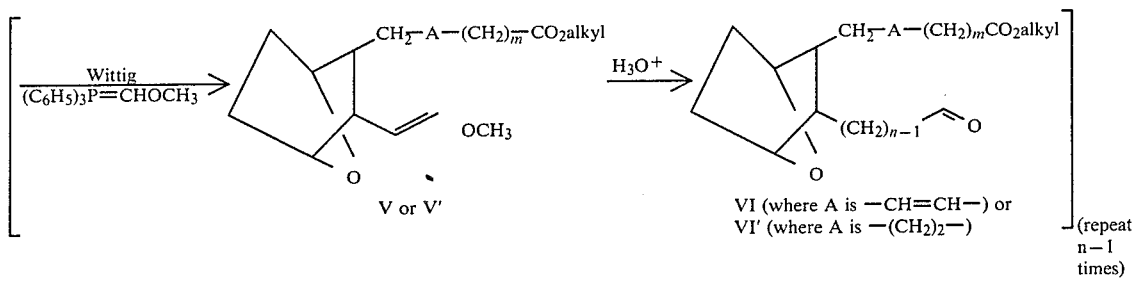
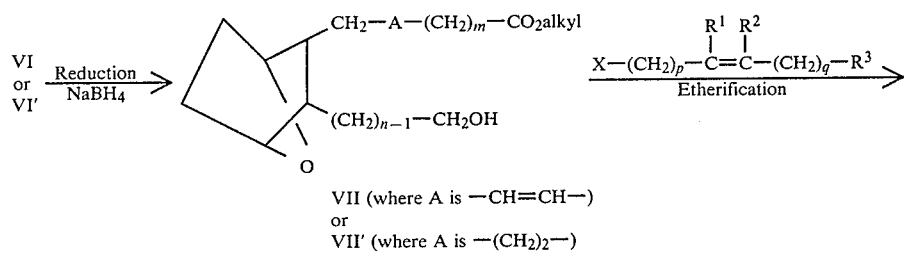
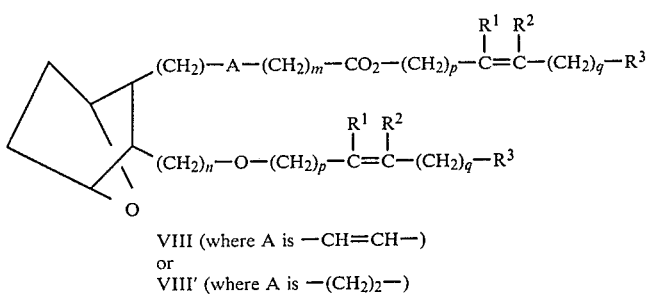
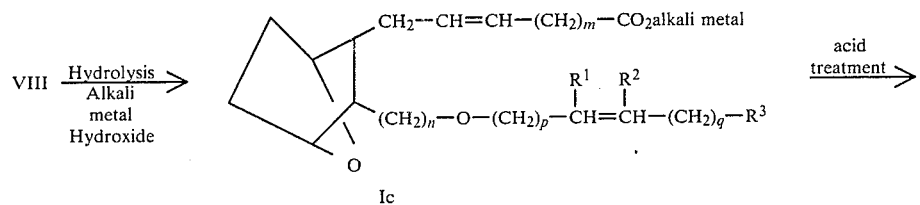

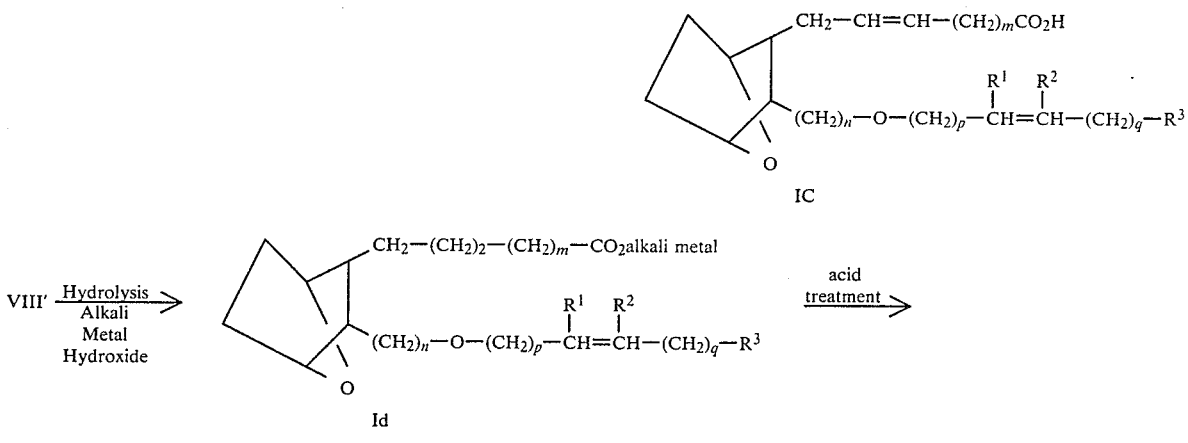

In the reaction sequence, identified as "A", where in Formula I n is 1, the lower alkyl ester containing the hydroxymethyl group, that is, compound II (where A is —CH=CH—) or IIA (where A is —(CH$_2$)$_2$) (prepared as described in U.S. Pat. No. 4,143,054) is employed as the starting material. Thus, where A is —CH=CH—, compound II is subjected to an etherification reaction, for example, by reacting a compound of the structure

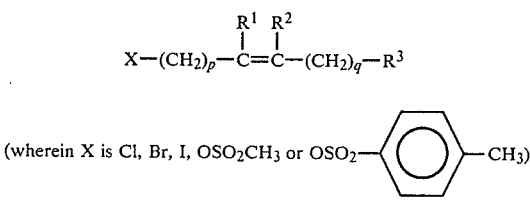

in the presence of a strong inorganic base such as KOH or NaOH, and an appropriate solvent to form ester III. To form the ester IIIA (where A is (CH$_2$)$_2$), (Reaction sequence "B"), compound II is reduced, for example, with hydrogen over a palladium on carbon catalyst, to form hydroxymethyl compound IIA (where A is (CH$_2$)$_2$) and compound IIA is subjected to an etherification reaction as described above to form ester IIIA (where A is (CH$_2$)$_2$). In carrying out the above reaction, the hydroxymethyl compound II or IIA is employed in a molar ratio to the halide A, that is, II or IIA:A, of within the range of from about 0.8:1 to about 1:5, employing a solvent such as xylene, tetrahydrofuran (THF), dimethylsulfoxide (DMSO) or dimethyl formamide (DMF). Where in the formula A starting material, X is Br or Cl, a phase transfer etherification is employed in which case THF is used as the solvent and a phase transfer reagent such as Bu$_4$NHSO$_4$, or (C$_6$H$_5$CH$_2$)(CH$_3$)$_2$NHSO$_4$ is employed.

In the reaction sequence identified as "C", where in Formula I n is 2 to 4, the starting lower alkyl ester containing the hydroxymethyl group, that is, compound II, (prepared as described in U.S. Pat. No. 4,143,054) is used to form the aldehyde IV (where A is —CH=CH—) or IV' (where A is —(CH$_2$)$_2$). Thus, to form aldehyde IV where A is —CH=CH—, compound II is subjected to a Collins oxidation, for example, by reacting II with chromium trioxide in pyridine. To form the aldehyde IV' (where A is (CH$_2$)$_2$), compound II is reduced, for example, with hydrogen over a palladium on carbon catalyst, to form hydroxymethyl compound IIA (where A is (CH$_2$)$_2$) and compound IIA is subjected to a Collins oxidation to form aldehyde IV' (where A is (CH$_2$)$_2$).

The aldehyde IV or IV' is used to prepared aldehyde VI or VI' (where n is 2-4) carrying out a homologation sequence, such as a Wittig reaction with (C$_6$H$_5$)$_3$P=CHOMe followed by hydrolysis, (n−1) times. The aldehyde VI or VI' (where n is 2-4) is thus carried on to compounds of this invention where n is 2-4, that is

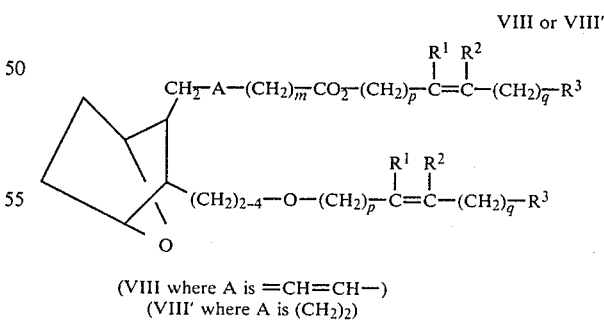

(VIII where A is =CH=CH—)
(VIII' where A is (CH$_2$)$_2$)

by reducing aldehyde VI or VI' employing a reducing agent such as sodium borohydride or sodium cyanoborohydride in a solvent such as methanol to form the alcohol ester VII or VII' which is subjected to an etherification reaction as described above to form VIII or VIII'.

The esters III, IIIA, VIII or VIII' can be converted to the free acid, that is, to I (A is —CH=CH) or
I' (A is (CH$_2$)$_2$)

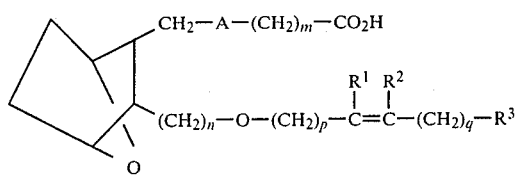

by treating the esters with an alkali metal hydroxide, such as lithium or sodium hydroxide to form the alkali metal salt Ia or Ib or Ic or Id, followed by neutralization with an acid, such as dilute hydrochloric acid or oxallic acid to form the acid IA, IB, IC or ID.

The tris(hydroxymethyl)aminomethane salt of any of the acids of formula I of the present invention is formed by reacting a solution of such acid in an inert solvent such as methanol with tris(hydroxymethyl)aminomethane and thereafter the solvent is removed by evaporation to leave the desired salt.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials and following the procedures as outlined in U.S. Pat. No. 4,143,054. Examples of such stereoisomers are set out below.

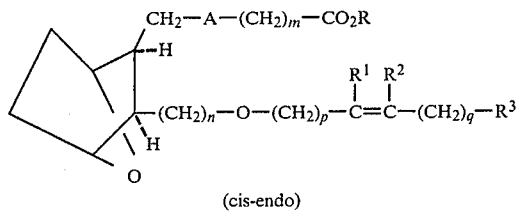

(cis-endo)

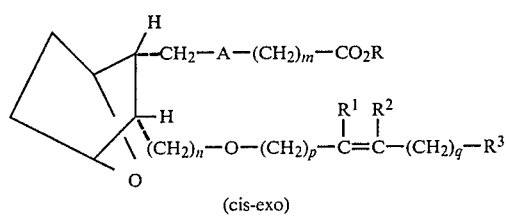

(cis-exo)

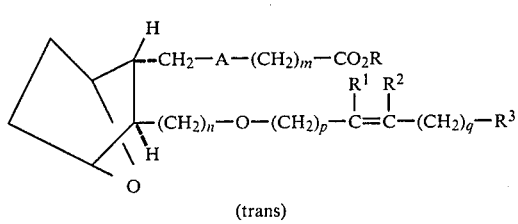

(trans)

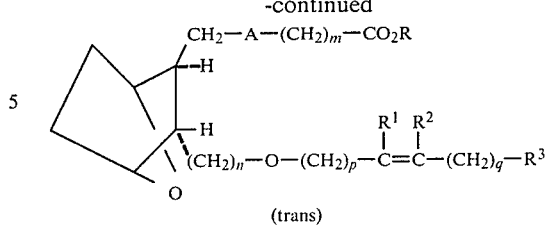

(trans)

The nucleus in each of the compounds of the invention is depicted as

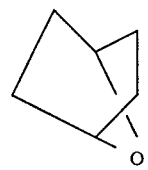

for matter of convenience; it will also be appreciated that the nucleus in the compounds of the invention may be depicted as

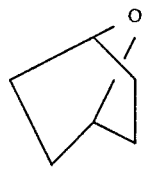

The compounds of this invention are cardiovascular agents useful as platelet aggregation inhibitors such as inhibiting arachidonic acid-induced platelet aggregation, e.g., for treatment of thrombolytic disease, such as coronary or cerebral thromboses or as inhibitors of bronchoconstriction associated with asthma. They are also selective thromboxane A$_2$ receptor antagonists and synthetase inhibitors, e.g., having a vasodilatory effect for treatment of myocardial ischemic disease, such as angina pectoris. The compounds of the invention are also arachidonic acid cyclooxygenase inhibitors and are useful as analgesic agents in the manner of aspirin and indomethacin. In addition, the compounds of the invention are useful as antiinflammatory agents in the manner of indomethacin and phenylbutazone as indicated by carragenin-induced edema in the rat [Ref: Winter et al, J. Pharmacol., Exp. Ther. 141:369, 1963] and they may be used to decrease joint swelling, tenderness, pain and stiffness in conditions such as rheumatoid arthritis. The compounds of the invention can be administered orally or parenterally to various mammalian species known to be subject to such maladies, e.g., cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of the present invention. Unless otherwise indicated, all temperatures are expressed in degrees Centigrade.

EXAMPLE 1

[1β,2α(Z),3α(E),4β]-7-[3-[(2-Hexenyloxy)methyl]-7-oxabicyclo[2.2.1]hept-2-yl]-5-heptenoic acid, 2-hexenyl ester

A.

[1β,2α(5Z),3α,4β]-7-[3-(Hydroxymethyl)-7-oxabicyclo[2.2.1]hept-2-yl]-5-heptenoic acid, methyl ester (a) A mixture of N-acetylpyridinium chloride was prepared by adding 9.6 ml (136 mmole) of acetyl chloride dropwise to 56 ml of pyridine. To this was added 5.0 g (27 mmole) of (exo)-3-(2-methoxyethenyl)-7-oxabicyclo[2.2.1]heptane-2-methanol dissolved in 5 ml of pyridine. The resulting mixture was stirred at room temperature for 1.5 hours and poured into brine. The product was extracted into ether (3×200 ml.); the ether extracts were washed with 5% hydrochloric acid (2×400 ml) and brine (1×200 ml) and dried over sodium sulfate. Concentration yielded a yellow oil which was purified by passage through a short column of silica gel (150 ml) with dichloromethane: yield 4.42 g of an oil.

(b) To a solution of 4.42 g (19.6 mmole) of the oil in 500 ml of tetrahydrofuran containing 50 ml of water was added 31.1 g (97.8 mmole) of mercuric acetate. The yellow suspension which formed was stirred for 10 minutes and then the entire mixture was poured into a solution containing 200 g of potassium iodide in 2 l. of water. Upon shaking, the yellow color disappeared and the mixture was extracted with benzene (3×500 ml). The combined benzene extracts were washed with potassium iodide solution and brine and dried over sodium sulfate. Concentration yielded 3.7 g of material which crystallized on standing in an ice box.

(c) A Wittig reagent was prepared in dimethyl sulfoxide (dried over calcium hydride) by adding a solution of sodium methylsulfinylmethide (prepared by heating 300 mg of sodium hydride in 60 ml of dimethyl sulfoxide at 75° until hydrogen evolution stops) dropwise to a solution of 5.32 g (12 mmole) of 4-carboxybutyl triphenylphosphonium bromide in 100 ml of dimethyl sulfoxide. After the first orange color lasting more than 10 seconds formed, an equivalent amount of base was added to form the ylide. To this deep orange solution was added a solution of the product of part (b) in 20 ml of dimethyl sulfoxide and the resulting mixture stirred at room temperature for 45 minutes. The reaction was quenched by addition of 24 mmole of acetic acid and the mixture poured into brine (300 ml) and extracted with ether (3×200 ml). Concentrations of these extracts gave an oil which was stirred with saturated sodium bicarbonate solution until crystalline triphenylphosphine oxide formed in the mixture. This mixture was washed with benzene and acidified with 10% hydrochloric acid. The aqueous layer was saturated with salt and extracted with ether which on drying (sodium sulfate) and concentration gave 2.43 g of crude product. The mixture was stirred 24 hours with 10% aqueous sodium hydroxide and reisolated by acidification and ether extraction. The product was purified on 500 g of silica gel with 50/50 ethyl acetate-hexane as the eluant which gave 600 mg of acid which crystallized on standing.

This was recrystallized twice from ethyl acetate-cyclohexane to yield 320 mg of [1β,2α(5Z),3α,4β]-7-[3-(hydroxymethyl)-7-oxabicyclo[2.2.1]hept-2-yl]-5-heptenoic acid.

(d) Following the procedure as set out in Example 7 of U.S. Pat. No. 4,143,054, the acid from part (c) is converted to the corresponding methyl ester.

B.

[1β,2α(Z),3α(E),4β]-7-[3-[(2-Hexenyloxy)methyl]-7-oxabicyclo[2.2.1]hept-2-yl]-5-heptenoic acid, 2-hexenyl ester A mixture of powdered KOH (0.56 g) in 14 ml of dry xylene was heated to reflux under argon atmosphere and 7 ml of xylene was removed by distillation. To this mixture was added a solution of 300 mg (1.12 mmol) of title A alcohol methyl ester in 10 ml of dry xylene. The volume of the reaction mixture was reduced 7 ml by distillative removal of xylene. To the reaction mixture was then added a solution of 1 g (5.60 mmol) E-1-hex-2-enylmesylate in 10 ml of dry xylene. This mixture was refluxed for 50 minutes at which time an additional 0.8 g of E-1-hex-2-enylmesylate was added. The mixture was refluxed for an additional 2 hours and 10 minutes. The cooled reaction mixture was diluted with 100 ml of saturated NaHCO$_3$ solution and extracted with CHCl$_3$ (5×100 ml). The combined CHCl$_3$ extracts were dried (MgSO$_4$), filtered and concentrated in vacuo. Purification was effected by flash chromatography on 37 g of silica gel 60 using hexane:ether (4:1) as eluant. This gave 345 mg of title B ester (74%) as a colorless oil. TLC: silica gel, 3:1 hexane-ether, R$_f$=0.60, iodine.

EXAMPLE 2

[1β,2α(Z),3α(E),4β]-7-[3-[(2-Hexenyloxy)methyl]-7-oxabicyclo[2.2.1]hept-2-yl]-5-heptenoic acid To a stirred solution of 345 mg (0.83 mmol) of the Example 1 ester, 36.0 ml of distilled THF, 3.00 ml of CH$_3$OH and 4.90 ml of H$_2$O under argon was added 9.20 ml of 1N aqueous lithium hydroxide solution. This mixture was purged with argon vigorously for 30 minutes and stirred at room temperature for 6.5 hours. The reaction mixture was acidified to pH 4 by addition of 1N aqueous HCl solution. The resulting solution was poured into 80 ml of saturated NaCl solution and was saturated with solid NaCl. The aqueous layer was extracted with EtOAc (4×100 ml). The combined EtOAc extracts were dried (MgSO$_4$), filtered and concentrated in vacuo. This was chromatographed on 30 g of silica gel 60 using 2% CH$_3$OH in CH$_2$Cl$_2$ as eluant to give 265 mg (97%) of pure title acid. TLC: silica gel, 2% CH$_3$OH/CH$_2$Cl$_2$, R$_f$=0.22, vanillin.

Anal. Calcd for C$_{20}$H$_{32}$O$_4$: C, 71.39; H, 9.59. Found: C, 71.01; H, 9.52.

EXAMPLE 3

[1β,2α(Z),3α(Z),4β]-7-[3-[(2-Hexenyloxy)methyl]-7-oxabicyclo[2.2.1]hept-2-yl]-5-heptenoic acid, 2-hexenyl ester A mixture of powdered KOH (0.56 g) in 15 ml of dry xylene was heated to reflux under argon atmosphere and 7 ml of xylene was removed by distillation. To this mixture was added a solution of 300 mg (1.12 mmol) of Example 1 part A alcohol methyl ester in 10 ml of dry xylene. The volume of the reaction mixture was reduced 7 ml by distillative removal of xylene. To the reaction mixture was then added a soution of 1 g (5.60 mmol) Z-1-hex-2-enylmesylate in 8 ml of dry xylene. This mixture was refluxed for 30 minutes at which time an additional 0.6 g of Z-1-hex-2-enylmesylate was added. The mixture was refluxed for an additional hour and 50 minutes. The cooled reaction mixture was diluted with 50 ml of saturated $NaHCO_3$ solution and extracted with $CH_2Cl_2$ (3×60 ml). The combined $CH_2Cl_2$ extracts were dried ($MgSO_4$), filtered and concentrated in vacuo. Purification was effected by flash chromatography on 36 g of silica gel 60 using hexane:ether (3:1) as eluant. This gave 0.34 g of title ester (73%) as a colorless oil. TLC: silica gel, hexane-ether (3:1), $R_f$=0.60, iodine.

EXAMPLE 4

[1β,2α(Z),3α(Z),4β]-7-[3-[(2-Hexenyloxy)methyl]-7-oxabicyclo[2.2.1]hept-2-yl]-5-heptenoic acid To a stirred solution of 340 mg (0.81 mmol) of Example 3 ester, 36.0 ml of distilled THF, 3 ml of $CH_3OH$ and 4.90 ml of $H_2O$ under argon was added 9.20 ml of 1N aqueous lithium hydroxide solution. This mixture was purged with argon vigorously for 30 minutes and stirred at room temperature for 6.5 hours. The reaction mixture was acidified to pH 4 by the addition of 1N aqueous HCl solution. The resulting solution was poured into 80 ml of saturated NaCl solution and was saturated with solid NaCl. The aqueous layer was extracted with EtOAc (4×100 ml). The combined EtOAc extracts were dried ($MgSO_4$), filtered and concentrated in vacuo. This was chromatographed on 30 g of silica gel 60 using 2% $CH_3OH$ in $CH_2Cl_2$ as eluant to give 254 mg (93%) of pure title acid. TLC: silica gel, 2% $CH_3OH/CH_2Cl_2$, $R_f$=0.22, vanillin.

Anal Calcd for $C_{20}H_{32}O_4$: C, 71.39; H, 9.59. Found: C, 70.97; H, 9.64.

EXAMPLE 5

(1β,2α,3α(E),4β)-7-[3-[(2-Hexenyloxy)methyl]-7-oxabicyclo[2.2.1]hept-2-yl]heptanoic acid, 2(E)-hexenyl ester

A.

(1β,2α,3α,4β)-7-[3-[(Hydroxy)methyl]-7-oxabicyclo[2.2.1]hept-2-yl]-heptanoic acid, methyl ester To 800 mg (3.0 mmole) of the [1β,2α(5Z),3α,4β]-7-[3-(hydroxymethyl)-7-oxabicyclo[2.2.1]hept-2-yl]-5-heptenoic acid, methyl ester as prepared in Example 1, dissolved in 120 ml of ethyl acetate was added, under an argon atmosphere, 160 mg of 5% Pd on carbon. The argon atmosphere was exchanged for a slight positive pressure of hydrogen and the reaction was stirred for 8 hours at 25° C., filtered through a celite plug and evaporated to provide 730 mg (90%) of the title A compound.

B.

(1β,2α,3α(E),4β)-7-[3-[(Hexenyloxy)methyl]-7-oxabicyclo[2.2.1]hept-2-yl]heptanoic acid, 2(E)-hexenyl ester Following the procedure of Example 1 except substituting the Part A alcohol-ester for the Example 1A alcohol ester, the title product is obtained.

EXAMPLE 6

(1β,2α,3α(E),4β)-7-[3-[(2-Hexenyloxy)methyl]-7-oxabicyclo[2.2.1]hept-2-yl]heptanoic acid Following the procedure of Example 2 except substituting the Example 5 hexenyl ester for the Example 1 hexenyl ester, the title acid is obtained.

EXAMPLE 7

[1β,2α(5Z),3β(E),4β]-7-[3-[(2-Hexenyloxy)methyl]-7-oxabicyclo[2.2.1]hept-2-yl]-5-heptenoic acid

A.

[1β,2α(5Z),3β,4β]-7-[3-(Hydroxymethyl)-7-oxabicyclo[2.2.1]hept-2-yl]-5-heptenoic acid, methyl ester To a solution of 2.68 g of Example 1, part A alcohol in 175 ml of dimethylformamide was added 13.16 g of pyridinium dichromate. This mixture was stirred at room temperature for 19 hours at which time an additional 8 g of pyridinium dichromate was added. This mixture was allowed to stir an additional 24 hours. The reaction mixture was diluted with 500 ml of ether and the resultant black gummy precipitate was removed by filtration through a pad of Celite. The filtrate was concentrated in vacuo. The resulting dark brown oil was passed through 60 g of silica gel 60 and eluted with 5% $MeOH/CH_2Cl_2$ to give 1.86 g of brown oil.

This was purified by chromatography on 150 g of silica gel 60 using 1:1:0.01 pentane-ether-acetic acid as eluant. This gave 0.63 g of [1β,2α(5Z),3α,4β]-7-[3-(carboxy)-7-oxabicyclo-[2.2.1]hept-2-yl]-5-heptenoic acid, methyl ester and 0.31 g of [1β,2α(5Z),3β,4β]-7-[3-(carboxy)-7-oxabicyclo[2.2.1]hept-2-yl]-5-heptenoic acid, methyl ester; $^{13}CNMR(CDCl_3$, 15.0 MHz) δ177.0, 174.0, 130.6, 127.7, 81.5, 77.9, 54.7, 51.3, 46.2, 33.4, 32.3, 29.2, 26.6, 25.8, 24.7.

A solution of 350 mg of [1β,2α(5Z),3β,4β]-7-[3-(carboxy)-7-oxabicyclo[2.2.1]hept-2-yl]-5-heptenoic acid, methyl ester acid and 0.35 ml of triethylamine in 3.0 ml of dry THF under Ar was cooled to 0° C. To this stirred solution was added dropwise 0.24 ml of ethylchloroformate. The resulting mixture was stirred at 0° C. for 50 minutes and then diluted with 20 ml of anhydrous ether. The mixture was filtered through a pad of $MgSO_4$ and concentrated in vacuo. The residue was dissolved in 2 ml of absolute EtOH and 3.3 ml of dry THF. This solution was cooled in an ice bath and then 80 mg of $NaBH_4$ was added. The mixture was stirred for 30 minutes at 0° C. and then the ice bath was removed. After 15 minutes, the reaction mixture was poured into 25 ml of ice-cold 1N HCl. The aqueous layer was extracted with three 25 ml portions of ether. The ether layers were combined, dried over $MgSO_4$, filtered, and concentrated in vacuo to afford the crude title A alcohol. Purification was effected by flash chromatography of 22 g of silica gel using 2% $MeOH/CH_2Cl_2$ as eluant. This gave 250 mg of title A alcohol; $^{13}C$ NMR ($CDCl_3$, 15.0 MHz) δ174.1, 130.0, 128.5, 80.6, 78.7, 63.4, 51.7, 51.4, 47.8, 33.4, 32.7, 29.8, 26.6, 24.7, 23.7.

B.

[1β,2α(5Z),3β(E),4β]-7-[3-[(2-Hexenyloxy)methyl]-7-oxabicyclo[2.2.1]hept-2-yl]-5-heptenoic acid Following the procedure of Examples 1 and 2 except substituting [1β,2α(5Z),3β,4β]-7-[3-(hydroxymethyl)-7-oxabicyclo[2.2.1]hept-2-yl]-5-heptenoic acid, methyl ester for [1β,2α(5Z),3α,4β]-7-[3-(hydroxymethyl)-7- oxabicyclo[2.2.1]hept-2-yl]-5-heptenoic acid, methyl ester, the title compound is obtained.

EXAMPLE 8

[1β,2α(5Z),3α(Z),4β]-7-[3-[(3-Hexenyloxy)methyl]-7-oxabicyclo[2.2.1]hept-2-yl]-5-heptenoic acid, 3(Z)-hexenyl ester A mixture of powdered KOH (0.56 g) in 15 ml dry xylene was heated to reflux under argon atmosphere and 7 ml of xylene was removed by distillation. To this mixture was added a solution of 310 mg (1.16 mmol) of alcohol methyl ester in 8 ml of dry xylene. The volume of the reaction mixture was reduced 8 ml by distillative removal of xylene. To the reaction mixture was then added a solution of 1.01 g (5.67 mmol) of cis-3-hexen-1-mesylate in 10 ml of dry xylene. This mixture was refluxed for 1 hour at which time an additional 1 ml of cis-3-hexen-1-mesylate was added. The mixture was refluxed for an additional 25 minutes. The cooled reaction mixture was diluted with 50 ml of saturated NaCl solution and extracted once with 70 ml of $CH_2Cl_2$, then with EtOAc (4×50 ml). The combined $CH_2Cl_2$ and EtOAc extracts were dried ($MgSO_4$), filtered and concentrated in vacuo. The residue was treated with 30 ml of $CH_2N_2$ solution and stirred at room temperature and concentrated in vacuo to remove excess $CH_2N_2$ and solvent. Purification was effected by flash chromatography on 34 g of silica gel 60 using hexane:ether (4:1) as eluant. This gave 180 mg of title hexenyl ester (37%) and 100 mg of a mixture band of corresponding methyl ester and title hexenyl ester (~23%). TLC=silica gel, 2:1 hexane-ether, $R_f$=0.60, iodine.

EXAMPLE 9

[1β,2α(5Z),3α(Z),4β]-7-[3-[(3-Hexenyloxy)methyl]-7-oxabicyclo[2.2.1]hept-2-yl]-5-heptenoic acid To a stirred solution of 180 mg (0.43 mmol) of Example 8 hexenyl ester, 22 ml of freshly distilled THF and 3.6 ml of $H_2O$ under argon was added 4.3 ml of 1N aqueous lithium hydroxide solution. This mixture was purged with argon vigorously for 20 minutes and stirred at room temperature for 8 hours and 30 minutes. The reaction mixture was diluted with 10 ml of freshly distilled THF and stirred for an hour at which time 3 ml of methanol was added. The reaction mixture was then stirred for another 5 hours and 30 minutes. The reaction mixture was acidified to pH 2 by the addition of 1N aqueous HCl solution. The resulting solution was poured into 50 ml of saturated NaCl solution and was saturated with solid NaCl. The aqueous layer was extracted with EtOAc (4×50 ml). The combined EtOAc extracts were dried ($MgSO_4$), filtered and concentrated in vacuo. This was chromatographed on 34 g of silica gel 60 using 3% $CH_3OH$ in $CH_2Cl_2$ as eluant to give 123 mg (84%) of pure title acid. TLC=silica gel, 4% $CH_3OH/CH_2Cl_2$, $R_f$=0.3, iodine.

Anal Calcd for $C_{20}H_{32}O_4$: C, 71.39; H, 9.59. Found: C, 71.10; H, 9.59.

EXAMPLE 10

[1β,2α(5Z),3β(E),4β]-7-[3-(2-Butenyloxy)methyl]-7-oxabicyclo[2.2.1]hept-2-yl]-5-heptenoic acid Following the procedure of Example 7 except substituting E-1-but-2-enylmesylate for E-1-hex-2-enylmesylate, the title compound is obtained.

EXAMPLE 11

(1β,2α,3α(E),4β)-7-[3-(4-Methyl-3-hexenyloxy)methyl]-7-oxabicyclo[2.2.1]hept-2-yl]heptanoic acid Following the procedure of Examples 5 and 6 except substituting E-4-methyl-hex-3-enyl methanesulfonate for E-1-hex-2-enylmesylate, the title compound is obtained.

EXAMPLE 12

[1β,2α(5Z),3α(Z),4β]-7-[3-(4-Octenyloxy)methyl]-7-oxabicyclo[2.2.1]hept-2-yl]-5-heptenoic acid Following the procedure of Examples 1 and 2 except substituting Z-oct-4-enyl methanesulfonate for E-1-hex-2-enylmesylate, the title compound is obtained.

EXAMPLE 13

[1β,2α(5Z),3α(E),4β]-7-[3-(6-Phenyl-2-hexenyloxy)methyl]-7-oxabicyclo[2.2.1]hept-2-yl]-5-heptenoic acid Following the procedure of Examples 1 and 2 except substituting E-6-phenyl-hex-2-enylmethanesulfonate for E-1-hex-2-enylmesylate, the title compound is obtained.

EXAMPLE 14

[1β,2α(5Z),3α(Z),4β]-7-[3-(5-Cyclohexyl-3-methyl-3-pentenyloxy)methyl]-7-oxabicyclo[2.2.1]hept-2-yl]-5-heptenoic acid Following the procedure of Examples 1 and 2 except substituting Z-5-cyclohexyl-3-methylpent-3-enyl methanesulfonate for E-1-hex-2-enylmesylate, the title compound is obtained.

EXAMPLE 15

[1β,2α(5Z),3β(E),4β]-7-[3-(6-Dodecenyloxy)methyl]-7-oxabicyclo[2.2.1]hept-2-yl]-5-heptenoic acid Following the procedure of Example 7 except substituting E-6-dodecenylmethanesulfonate for E-1-hex-2-enylmesylate, the title compound is obtained.

EXAMPLE 16

(1β,2α,3α(Z),4β)-7-[3-(10-Cyclopentyl-6-decenyloxy)methyl]-7-oxabicyclo[2.2.1]hept-2-yl]heptanoic acid Following the procedure of Examples 5 and 6 except substituting Z-10-cyclopentyldec-6-enyl methanesulfonate for E-1-hex-2-enylmesylate, the title compound is obtained.

EXAMPLE 17

[1β,2α(5Z),3α(Z),4β]-7-[3-(5-Cyclohexyl-3,4-dimethyl-3-pentenyloxy)methyl]-7-oxabicyclo[2.2.1]hept-2-yl]-5-heptenoic acid Following the procedure of Examples 1 and 2 except substituting Z-5-cyclohexyl-3,4-dimethylpent-3-enyl methanesulfonate for E-1-hex-2-enylmesylate, the title compound is obtained.

EXAMPLE 18

[1β,2α(5Z),3α,4β]-7-[3-[(2-Propenyloxy)methyl]-7-oxabicyclo[2.2.1]hept-2-yl]-5-heptenoic acid, methyl ester To a stirred solution of 310 mg (1.16 mmol) of Example 1, Part A ester alcohol in 1.34 ml of distilled THF was added in order, 1.34 ml (15.5 mmol) of allyl bromide, 107 mg (0.31 mmol) of tetrabutylammonium hydrogen sulfate and 1.34 ml of 50% aqueous sodium hydroxide solution. This mixture was stirred at room temperature in darkness for 23 hours. The reaction mixture was poured into 30 ml of saturated sodium bicarbonate solution and extracted with $CH_2Cl_2$ (3×30 ml). The combined $CH_2Cl_2$ extracts were dried ($MgSO_4$), filtered and concentrated in vacuo. Purification was effected by flash chromatography on 35 g of silica gel 60 using 2:1 hexane-ether as eluant to give 220 mg (62%) of title methyl ester. TLC: silica gel, 1:1 hexane-ether, $R_f$=0.4, iodine.

EXAMPLE 19

[1β,2α(5Z),3α,4β]-7-[3-[(2-Propenyloxy)methyl]-7-oxabicyclo[2.2.1]hept-2-yl]-5-heptenoic acid To a stirred solution of 220 mg (0.71 mmol) of Example 18 ester, a small amount of hydroquinone, 36 ml of distilled THF and 6.0 ml of $H_2O$ under argon was added 7.0 ml of 1N aqueous lithium hydroxide solution. This mixture was purged with argon vigorously for 30 minutes and stirred at room temperature for 5.5 hours. The reaction mixture was acidified to pH 3 by the addition of 1N aqueous HCl solution. The resulting solution was poured into 80 ml of saturated NaCl solution and was saturated with solid NaCl. The aqueous layer was extracted with EtOAc (4×125 ml). The combined EtOAc extracts were dried ($MgSO_4$), filtered and concentrated in vacuo. This was chromatographed on 30 g of silica gel 60 using 4% $CH_3OH$ in $CH_2Cl_2$ as eluant to give 190 mg (90%) of pure title acid, TLC: silica gel, 1:1 hexane-ether, $R_f$=0.15, iodine.

Anal Calcd for $C_{17}H_{26}O_4$: C, 69.36; H, 8.90. Found: C, 69.72; H, 9.05.

EXAMPLE 20

[1β,2α(Z),3α,4β]-7-[3-[(3-Butenylxoy)methyl]-7-oxabicyclo[2.2.1]hept-2-yl]-5-heptenoic acid Following the procedure of Examples 18 and 19 except substituting 3-butenyl bromide for allyl bromide, the title compound is obtained.

EXAMPLE 21

(1β,2α(Z),3α,4β)-7-[3-[(5-Hexenyloxy)methyl]-7-oxabicyclo[2.2.1]hept-2-yl]heptanoic acid Following the procedure of Examples 18, 19 and 2 except substituting the Example 5 part A methyl ester for the Example 1 methyl ester and substituting 5-hexenyl bromide for allyl bromide, the title compound is obtained.

EXAMPLE 22

[1β,2α(5Z),3α(E),4β]-7-[3-[2-(2-Hexenyloxy)ethyl]-7-oxabicyclo[2.2.1]hept-2-yl]-5-heptenoic acid

A.

[1β,2α(5Z),3α,4β]-7-[3-(2-Oxo)ethyl-7-oxabicyclo[2.2.1]hept-2-yl]-5-heptenoic acid, methyl ester Into a dry 100 ml round bottom 3-necked flask containing a stir bar was added dried 12.9 g (37.7 mmoles) methoxymethyltriphenylphosphonium chloride (($C_6H_5$)$_3$P$^+$—$CH_2OCH_3Cl^-$) and 235 ml distilled toluene (stored over molecular sieves). The resulting suspension was stirred in an ice-bath, under argon, until cold and then a 1.55M solution of 18.3 ml (28.3 mmol) of potassium t-amylate in toluene was added dropwise. A bright red solution formed which was stirred at 0° C. for an additional 35 minutes. Thereafter, a solution of 4.97 g (18.8 mmol) [1β,2α(5Z),3α,4β]-7-[3-formyl-7-oxabicyclo[2.2.1]hept-2-yl]-5-heptenoic acid, methyl ester in 60 ml toluene was added by means of a dropping funnel over a 35 minute period with the ice-bath still in place. The reaction was then quenched by addition of 2.3 g (39 mmol) acetic acid in 5 ml ether. The reaction mixture immediately turned pale yellow and was immediately poured into 200 ml saturated $NH_4Cl$, and extracted with ether (4×200 ml). The combined ether phases were washed with NaCl saturated solution, and dried ($MgSO_4$) and concentrated to yield a yellow oil in a white crystalline solid (phosphine oxide). The white solid was triturated with EtOAc and the mother liquor was purified by chromatography on an LPS-1 silica column. The fractions obtained were (A) [1β,2α(5Z),3α,4β]-7-[3-(2-oxo)ethyl-7-oxabicyclo[2.2.1]hept-2-yl]-5-heptenoic acid, methyl ester, (B) [1β,2α(5Z),3α,4β]-7-[3-(2-methoxy)ethendiyl]-7-oxabicyclo[2.2.1]hept-2-yl]-5-heptenoic acid, methyl ester, and (C) [1β,2α(5Z),3α,4β]-7-[3-(2,2-dimethoxy)ethyl-7-oxabicyclo[2.2.1]hept-2-yl]-5-heptenoic acid, methyl ester.

Compounds (B) and (C) are each treated with trifluoroacetic acid to convert each to compound (A).

B.

[1β,2α(5Z),3α,4β]-7-[3-(2-Hydroxyethyl)-7-oxabicyclo[2.2.1]hept-2-yl]-5-heptenoic acid, methyl ester The aldehyde (1.4 g, 5 mmol) from part A in methanol (50 ml) was treated with $NaBH_4$ (0.19 g, 5 mmol) in an argon atmosphere at 0° C. After stirring at 0° for 1 hour, the reaction was quenched by addition of 2N HCl (to pH 2). The methanol was removed in vacuo and the reaction mixture was taken up in ether. The ether solution was washed with saturated $KHCO_3$, saturated NaCl and dried ($MgSO_4$). The ether was evaporated to yield the title B compound.

C.

[1β,2α(5Z),3α(E),4β]-7-[3-[2-(2-Hexenyloxy)ethyl]-7-oxabicyclo[2.2.1]hept-2-yl]-5-heptenoic acid Following the procedure of Examples 1 and 2 except substituting the above part B alcohol for the alcohol in Example 1, part A, the title compound is obtained.

EXAMPLE 23

[1β,2α(5Z),3β(E),4β]-7-[3-[2-(2-Hexenyloxy)ethyl]-7-oxabicyclo[2.2.1]hept-2-yl]-5-heptenoic acid Following the procedure of Example 22, except substituting [1β,2α(5Z),3β,4β]-7-[3-formyl-7-oxabicyclo[2.2.1]hept-2-yl]-5-heptenoic acid, methyl ester for [1β,2α(5Z),3α,4β]-7-[3-formyl-7-oxabicyclo[2.2.1]hept-2-yl]-5-heptenoic acid, methyl ester, the title compound is obtained.

EXAMPLE 24

(1β,2α,3α(E),4β)-7-[3-[2-(2-Hexenyloxy)ethyl]-7-oxabicyclo[2.2.1]hept-2-yl]heptanoic acid Following the procedure of Example 23 except substituting (1β,2α,3α,4β)-7-[3-formyl-7-oxabicyclo[2.2.1]hept-2-yl]heptanoic acid, methyl ester for [1β,2α(5Z),3β,4β]-7-[3-formyl-7-oxabicyclo[2.2.1]hept-2-yl]-5-heptenoic acid, methyl ester, the title compound is obtained.

EXAMPLE 25

[1β,2α(5Z),3α(Z),4β]-7-[3-[2-(7-Phenyl-3-heptenyloxy)ethyl]-7-oxabicyclo[2.2.1]hept-2-yl]-5-heptenoic acid Following the procedure of Example 22 except substituting Z-7-phenylhept-3-enyl methanesulfonate for E-1-hex-2-enylmesylate, the title compound is obtained.

EXAMPLE 26

[1β,2α(5Z),3β(E),4β]-7-[3-[2-(9-Cyclopropyl-4-methyl-4-nonenyloxy)ethyl]-7-oxabicyclo[2.2.1]hept-2-yl]-5-heptenoic acid Following the procedure of Example 23 except substituting E-9-cyclopropyl-4-nethyl non-4-enyl methanesulfonate for E-1-hex-2-enylmesylate, the title compound is obtained.

EXAMPLE 27

[1β,2α(5Z),3α(E),4β]-7-[3-[4-(2-Hexenyloxy)butyl]-7-oxabicyclo[2.2.1]hept-2-yl]-5-heptenoic acid

A.
[1β,2α(5Z),3α,4β]-7-[3-(3-Oxo)propyl-7-oxabicyclo[2.2.1]hept-2-yl]-5-heptenoic acid, methyl ester Following the procedure of Example 22, part A except substituting [1β,2α(5Z),3α,4β]-7-[3-(2-oxo)ethyl-7-oxabicyclo[2.2.1]hept-2-yl]-5-heptenoic acid, methyl ester for [1β,2α(5Z),3α,4β]-7-[3-formyl-7-oxabicyclo[2.2.1]hept-2-yl]-5-heptenoic acid, methyl ester, the title compound is obtained.

B.
[1β,2α(5Z),3α,4β]-7-[3-(4-Oxo)butyl-7-oxabicyclo[2.2.1]hept-2-yl]-5-heptenoic acid, methyl ester Following the procedure of Example 18, part A, except substituting the aldehyde from part A above, for [1β,2α(5Z),3α,4β]-7-[3-formyl-7-oxabicyclo[2.2.1]hept-2-yl]-5-heptenoic acid, methyl ester, the title B aldehyde is obtained.

C.
[1β,2α(5Z),3α,4β]-7-[3-(4-Hydroxybutyl)-7-oxabicyclo[2.2.1]hept-2-yl]-5-heptenoic acid, methyl ester Following the procedure of Example 18, part B, except substituting the title B aldehyde for [1β,2α(5Z),3α,4β]-7-[3-(2-oxo)ethyl-7-oxabicyclo[2.2.1]hept-2-yl]-5-heptenoic acid, methyl ester, the title C alcohol is obtained.

D. [1β,2α(5Z),3α(E),4β]-7L-[3-[4-(2-Hexenyloxy)butyl]-7-oxabicyclo-[2.2.1]hept-2-yl]-5-heptenoic acid Following the procedure of Examples 1 and 2 except substituting the above part C alcohol for the alcohol used in Example 1, part A, the title compound is obtained.

EXAMPLE 28

[1β,2α(5Z),3α(Z),4β]-7-[3-[4-(8-Cyclohexyl-5-octenyloxy)butyl]-7-oxabicyclo[2.2.1]hept-2-yl]-5-heptenoic acid Following the procedure of Example 27 except substituting Z-8-cyclohexyl oct-5-enyl methanesulfonate for E-1-hex-2-enylmesylate, the title compound is obtained.

EXAMPLE 29

[1β,2α(5Z),3α(E),4β]-7-[3-[4-(7-Phenyl-2-heptenyloxy)butyl]-7-oxabicyclo[2.2.1]hept-2-yl]-5-heptenoic acid Following the procedure of Example 27 except substituting E-7-phenylhept-2-enyl methanesulfonate for E-1-hex-2-enylmesylate, the title compound is obtained.

EXAMPLE 30

[1β,2β(5Z),3α,4β]-7-[3-[(2-Hexenyloxy)methyl]-7-oxabicyclo[2.2.1]hept-2-yl]-5-heptenoic acid, methyl ester

A.
(1β,2α,3α,4β)-cis-exo-2-Formyl-3-isopropyloxycarbonyloxymethyl-7-oxabicyclo[2.2.1]heptane To a suspension of 11.4 g lithium aluminum hydride (300 mmole, 1.6 eq) in 400 ml of dry THF at 0° C. was added dropwise a solution of 32 g of (exo)hexahydro-4,7-epoxyisobenzofuran-1,3-dione (cis-exo-aldehyde), prepared as described in Example 1 of U.S. Pat. No. 4,143,054 (190 mmole) in 400 ml of dry THF over a period of 1 hour. The reaction mixture was stirred at 25° C. for 18 hours, cooled to 0° C. and quenched by slow addition of a saturated $Na_2SO_4$ solution, and filtered. The solid was washed with three 100 ml portions of $CH_2Cl_2$. THe combined organic layer was dried over $MgSO_4$ and concentrated to give 32 g of (1β,2α,3α,4β)-cis-exo-7-oxabicyclo[2.2.1]heptane 2,3-dimethanol as a colorless solid.

To a solution of 10 g of the above diol (63.2 mmole) in 40 ml dry THF at 0° C. was added with stirring 55 ml of a 12.5% by weight solution of phosgene in toluene (63.2 mmole, 1 eq.) dropwise over a period of 30 minutes. Argon was then bubbled through the reaction mixture for 15 minutes. The mixture was concentrated to give (1β,2α,3α,4β)-cis-exo-2-hydroxymethyl-3-chlorocarbonyloxymethyl-7-oxabicyclo[2.2.1]heptane in the form of a crude oil.

The above oil was dissolved in 30 ml of dry $CH_2Cl_2$ and cooled to −50° C. To this solution was added dropwise a solution of 10 ml pyridine in 10 ml $CH_2Cl_2$. THe mixture was stirred for 10 minutes and quenched with $H_2O$. THe mixture was then extracted thoroughly with $CH_2Cl_2$. The organic extract was dried over $MgSO_4$ and concentrated to give (1β,2α,3α,4β)-cis-exo-7-oxabicycl[2.2.1]-heptane 2,3-dimethanol carbonate as a crystalline solid (10.7 g).

A mixture of 10.7 g of the above cyclic carbonate (58.1 mmole) in 100 ml isopropanol was refluxed for 24 hours. Excess isopropanol was removed under reduced pressure to give 14.4 g (1β,2α,3α,4β)-cis-exo-2-hydroxymethyl-3-isopropyloxycarbonyloxymethyl-7-oxabicyclo[2.2.1]heptane as a viscous oil.

To a mechanically stirred suspension of 18.02 g of pyridinium chlorochromate in 112 ml of dry $CH_2Cl_2$ was added a solution of 12.02 g of (1β,2α,3α,4β)-cis-exo-2-hydroxymethyl-3-isopropyloxycarbonyloxymethyl-7-oxabicyclo[2.2.1]heptane in 12 ml of $CH_2Cl_2$ in one portion. The mixture was stirred for 90 minutes at room temperature and then diluted with 120 ml of ether.The supernatant liquid was decanted off and the gummy residue was washed with three 70 ml portions of ether. The combined organic solutions were passed through a short pad of Florosil ® and the filter cake washed with five 50 ml portions of ether. The filtrates were concentrated in vacuo to afford 10.12 g (85%) of (1β,2α,3α,4β)-cis-exo-2-formyl-3-isopropyloxycarbonyloxymethyl-7-oxabicyclo[2.2.1]heptane $^{13}$C NMR (CDCl$_3$, 15.0 MHz)δ201.0, 154.0, 77.8, 77.1, 72.1, 65.8, 57.6, 47.3, 29.1, 28.8, 21.5.

B.

(1β,2β,3α,4β)-2-Formyl-3-isopropyloxycarbonyloxymethyl-7-oxabicyclo[2.2.1]heptane A solution of 10.12 g of the above aldehyde in 170 ml of MeOH was cooled in an ice-bath under argon. To this stirred solution was added 0.85 g of NaOCH$_3$. After 15 minutes, the ice-bath was removed and the mixture was allowed to warm to room temperature over 2 hours. The volume of the reaction mixture was reduced 50% in vacuo and then poured into 500 ml of saturated NH$_4$Cl solution. This was extracted with three 200 ml portions of ether. The combined ether extracts were washed with 200 ml of brine, dried over MgSO$_4$, filtered, and concentrated in vacuo to give 10.4 g of wet crude product. Azeotropic removal of water with CH$_2$Cl$_2$ gave 6.19 g (61%) of title compound as a mixture of the isopropyl and methyl carbonates; $^{13}$C NMR (CDCl$_3$, 15.0 MHz)δ 199.4, 154.3, 79.1, 76.6, 71.9, 68.2, 59.1, 53.2, 43.3, 28.8, 26.0, 21.5.

C.

(1β,2β,3α,4β)-2-(2-Methoxyethenyl)-3-isopropyloxycarbonyloxymethyl-7-oxabicyclo[2.2.1]heptane To a stirred slurry of 11.28 g of (methoxymethyl)triphenylphosphonium chloride at −15° C. was added dropwise 19.9 ml of 1.42M KOt-amylate in toluene over 10 minutes. The reaction mixture was stirred 10 minutes and then placed in a 0° C. bath. To this burgundy red solution was added dropwise a solution of 5.69 g of title B aldehyde in 34 ml of THF over 2 hours, 40 minutes. The reaction mixture was allowed to warm to room temperature and stirred for 16 hours. The mixture was then cooled to −15° C. and 11.4 ml of acetaldehyde was added slowly. After stirring for 30 minutes, the mixture was poured into 250 ml of half-saturated NH$_4$Cl and extracted with three 250 ml portions of ether. The combined ether extracts were dried over MgSO$_4$, filtered, and concentrated in vacuo to afford the crude product. This was chromatographed on 150 g of silica gel using 1% CH$_3$OH, CH$_2$Cl$_2$ as eluant to give two mixed collections containing title compound C, 2.1 g and 4.2 g. The latter was triturated in hexane to give 1.62 g of the title enol ether, $^{13}$C NMR (CDCl$_3$, 15.0 MHz)δ 149.0, 148.4, 104.3, 101.0, 80.4, 79.3, 78.6, 71.7, 69.0, 68.5, 56.1, 49.9, 44.7, 29.5, 24.3, 23.9, 21.6.

D.

(1β,2β,3α,4β)-2-(Formylmethyl-3-isopropyloxycarbonyloxymethyl-7-oxabicyclo[2.2.1]heptane To a stirred solution of 3.72 g of the title C enol ether in 75 ml of THF was added 298 ml of 20% trifluoroacetic acid. After being stirred at room temperature for 6½ hours, the reaction mixture was neutralized to pH=70 with solid NaHCO$_3$. The THF was removed in vacuo and the aqueous layer was extracted with three 300 ml portions of ether. The combined ether extracts were dried over MgSO$_4$, filtered, and concentrated in vacuo to afford the crude title D aldehyde; $^{13}$C NMR (CDCl$_3$, 15.0 MHz)δ 200.5, 154.3, 78.8, 78.5, 71.8, 68.8, 49.3, 45.2, 38.8, 29.1, 23.8, 21.5.

E.

[1β,2β(5Z),3α,4β]-7-[3-(Hydroxymethyl)-7-oxabicyclo[2.2.1]hept-2-yl]-5-heptenoic acid To a stirred slurry of 9.16 g of 4-carboxybutyl)triphenylphosphonium bromide in 150 ml of toluene at −15° C. was added dropwise 26 ml of 1.42M KOt-amylate in toluene. The cold bath was removed and on warming to room temperature an additional 1.56 ml of 1.42M KOt-amylate in toluene was added. This was stirred for 1 hour and then a solution of 3.78 g of the above crude title D aldehyde in 30 ml of toluene was added slowly. This reaction mixture was stirred overnight at room temperature, then cooled to 0° C. and a solution of 5 ml HOAc in toluene (5 ml) was added. The resulting mixture was poured into 200 ml of saturated NH$_4$Cl and 200 ml EtOAc. The aqueous layer was acidified to pH=3.5-4.0, and extracted with three 200 ml portions of EtOAc. The combined EtOAc extracts were dried (MgSO$_4$), filtered, and concentrated in vacuo. The residue was triturated with 150 ml of isopropyl ether in an ice bath to give a sticky solid. The solution was decanted off and concentrated in vacuo to give 4.5 g of crude title E acid.

F.

[1β,2β(5Z),3α,4β]-7-[3-(Hydroxymethyl)-7-oxabicyclo[2.2.1]hept-2-yl]-5-heptenoic acid, methyl ester To a solution of 4.5 g of crude title E acid in 25 ml MeOH was added 2.25 g of dried, powdered Amberlyst 15 resin. The mixture was stirred at room temperature for 3½ days, then diluted with 26 ml of ether and filtered through a pad of Celite. The Celite pad was washed repeatedly with ether. The filtrate was dried over MgSO$_4$, filtered and concentrated in vacuo to give 2.86 g crude product. Repeated chromatography of this material afforded 0.34 g of title I ester; $^{13}$C NMR (CDCl$_3$, 15.0 MHz)δ 173.9, 129.3, 128.5, 79.2, 78.9, 65.0, 52.5, 45.4, 33.2, 29.6, 28.6, 26.5, 24.5, 23.7; along with the numerous impure fractions containing small amounts of the title ester.

G.

[1β,2β(5Z),3α,4β]-7-[3-[(2-Hexenyloxy)methyl]-7-oxabicyclo[2.2.1]hept-2-yl]-5-heptenoic acid Following the procedure of Examples 1 and 2 except substituting the title F alcohol methyl ester for Example 1 Part A alcohol methyl ester, the title product is obtained.

EXAMPLE 31

Tris(hydroxymethyl)aminomethane salt of [1β,2α(5Z),3α(E),4β]-7-[3-[(2-Hexenyloxy)methyl]-7-oxabicyclo[2.2.1]hept-2-yl]-5-heptenoic acid A solution of the compound formed in Example 2 in methanol is treated with an equivalent amount of tri(hydroxymethyl)aminomethane. The solvent is removed by evaporation to yield the title compound.

What is claimed is:

1. A compound having the structure formula

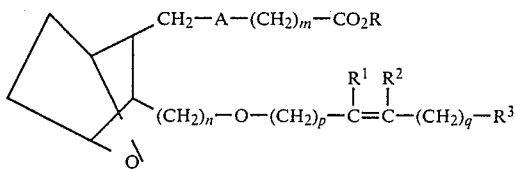

and including all stereoisomers thereof, wherein

A is —CH=CH— or —(CH$_2$)$_2$—;

m is 1 to 8; n is 1 to 4; p is 1 to 12; q is 0 to 5;

R is hydrogen, lower alkyl, hexenyl, alkali metal or tri(hydroxymethyl)aminomethane; R$^1$ and R$^2$ may be the same or different and are hydrogen or lower alkyl; and R$^3$ is hydrogen, lower alkyl, aryl or cycloalkyl; wherein the term lower alkyl or alkyl by itself or as part of another group contains 1 to 12 carbons and is unsubstituted or substituted with halo, trifluoromethyl, alkoxy, aryl, alkyl-aryl, halo-aryl, cycloalkyl or alkylcycloalkyl;

the term aryl by itself or as part of another group contains 6 to 10 carbons and is unsubstituted or substituted with lower alkyl, halogen or lower alkoxy;

the term cycloalkyl by itself or as part of another group contains 3 to 12 carbons and is unsubstituted or substituted with 1 or 2 halogens, 1 or 2 lower alkyl groups and/or 1 or 2 lower alkoxy groups; and (CH$_2$)$_m$, (CH$_2$)$_n$, (CH$_2$)$_p$ and (CH$_2$)$_q$ may be unsubstituted or include one or more alkyl substituents.

2. The compound as defined in claim 1 wherein A is —CH=CH—.

3. The compound as defined in claim 1 wherein R is H.

4. The compound as defined in claim 1 wherein n is 1.

5. The compound as defined in claim 1 wherein n is 2, 3 or 4.

6. The compound as defined in claim 1 wherein p is 1 and (CH$_2$)$_q$—R$^3$ is lower alkyl.

7. The compound as defined in claim 1 wherein A is —CH=CH—, m is 2 to 4, n is 1 or 2, p is 1 or 2, q is 1 or 2, R is H, R$^1$ and R$^2$ are each H, and R$^3$ is lower alkyl or cycloalkyl.

8. The compound as defined in claim 1 wherein A is —CH=CH—, m is 3, n is 1, p is 1, q is 1, R is H or 2-hexenyl, R$^1$ and R$^2$ are each H, and R$^3$ is lower alkyl.

9. The compound as defined in claim 1 wherein q is 0 and R$^3$ is H.

10. The compound as defined in claim 1 having the name [1β,2α(5Z),3α(E),4β]-7-[3-[(2-hexenyloxy)methyl]-7-oxabicyclo[2.2.1]hept-2-yl]-5-heptenoic acid or its 2-hexenyl ester, including all stereoisomers thereof.

11. The compound as defined in claim 1 having the name [1β,2α(5Z),3α(Z),4β]-7-[3-[(2-hexenyloxy)methyl]-7-oxabicyclo[2.2.1]hept-2-yl]-5-heptenoic acid or its 2-hexenyl ester, including all stereoisomers thereof.

12. The compound as defined in claim 1 having the name [1β,2α(5Z),3α,4β]-7-[3-[(2-propenyloxy)methyl]-7-oxabicyclo[2.2.1]hept-2-yl]-5-heptenoic acid or its methyl ester, including all stereoisomers thereof.

13. The compound as defined in claim 1 having the name [1β,2α(5Z),3α(Z),4β]-7-[3-[(3-hexenyloxy]methyl]-7-oxabicyclo[2.2.1]hept-2-yl]-5-heptenoic acid or its 3-hexenyl ester, including all stereoisomers thereof.

14. A method of inhibiting platelet aggregation and bronchoconstriction, which comprises administering to the circulatory system of a mammalian host an effective amount of a compound as defined in claim 1 or a pharmaceutically acceptable salt thereof.

15. The method as defined in claim 14 wherein said compound is administered in an amount within the range of from about 1 to about 100 mg/kg.

16. A composition for inhibiting platelet aggregation and bronchoconstriction comprising an effective amount of a compound as defined in claim 1 or a pharmaceutically acceptable salt thereof, and a pharmaceutically acceptable carrier thereof.

17. A method of inhibiting platelet aggregation which comprises administering to a mammalian host an effective amount of a compound as defined in claim 1 or a pharmaceutically acceptable salt thereof.

18. A method of inhibiting bronchoconstriction associated with asthma, which comprises administering to a mammalian host an effective amount of a compound as defined in claim 1 or a pharmaceutically acceptable salt thereof.

19. A method for inhibiting platelet aggregation and bronchoconstriction by inhibiting production of thromboxane A$_2$ by blocking the action of thromboxane synthetase, which comprises administering to a mammalian host an effective amount of a compound as defined in claim 1 or a pharmaceutically acceptable salt thereof.

20. A method for treating inflammation in a mammalian species in need of such treatment, which comprises administering to a mammalian host an effective amount of a compound as defined in claim 1 or a pharmaceutically acceptable salt thereof.

21. A method of relieving pain in a mammalian species which comprises administering to said mammalian species a composition containing an analgesically effective amount of a compound as defined in claim 1 or a pharmaceutically acceptable salt thereof.

* * * * *

UNITED STATES PATENT AND TRADEMARK OFFICE
CERTIFICATE OF CORRECTION

PATENT NO. : 4,526,900

DATED : July 2, 1985

INVENTOR(S) : Steven E. Hall et al.

It is certified that error appears in the above—identified patent and that said Letters Patent is hereby corrected as shown below:

Column 11, line 56, "Concentrations" should read
  --Concentration--.
Column 19, line 51, "7L" should read --7--.
Column 22, line 1 of claim 1, "structure" should read
  --structural--.

Signed and Sealed this

Twenty-ninth Day of October 1985

[SEAL]

Attest:

Attesting Officer

DONALD J. QUIGG

Commissioner of Patents and
Trademarks—Designate